(12) United States Patent
Pizzochero et al.

(10) Patent No.: US 11,383,028 B2
(45) Date of Patent: Jul. 12, 2022

(54) PLATE WITH INTEGRAL FLUID PATH CHANNELS

(71) Applicant: Becton, Dickinson and Company, Franklin Lakes, NJ (US)

(72) Inventors: Alessandro Egidio Pizzochero, Chelmsford, MA (US); J. Richard Gyory, Sudbury, MA (US); Joseph Biehler, Sparta, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 227 days.

(21) Appl. No.: 16/568,976

(22) Filed: Sep. 12, 2019

(65) Prior Publication Data

US 2020/0001006 A1    Jan. 2, 2020

Related U.S. Application Data

(62) Division of application No. 15/509,926, filed as application No. PCT/US2015/051188 on Sep. 21, 2015, now Pat. No. 10,449,292.

(60) Provisional application No. 62/053,674, filed on Sep. 22, 2014.

(51) Int. Cl.
*A61M 5/14* (2006.01)
*A61M 5/142* (2006.01)
*A61M 5/168* (2006.01)

(52) U.S. Cl.
CPC .... *A61M 5/14248* (2013.01); *A61M 5/16831* (2013.01); *A61M 2005/14252* (2013.01); *A61M 2005/14264* (2013.01); *A61M 2005/16863* (2013.01); *A61M 2205/332* (2013.01); *A61M 2205/3337* (2013.01); *A61M 2205/3341* (2013.01); *A61M 2205/3592* (2013.01); *A61M 2205/50* (2013.01); *A61M 2205/502* (2013.01); *A61M 2205/505* (2013.01); *A61M 2205/8206* (2013.01)

(58) Field of Classification Search
CPC .... A61M 5/14248; A61M 2005/14252; A61M 2005/14256; A61M 2005/1426
See application file for complete search history.

(56) References Cited

U.S. PATENT DOCUMENTS

| | | | |
|---|---|---|---|
| 3,930,500 A * | 1/1976 | Mohrke | B65D 75/5822 604/403 |
| 4,013,074 A | 3/1977 | Siposs | |
| 4,626,244 A | 12/1986 | Reinicke | |
| 4,747,832 A | 5/1988 | Buffet | |
| 4,816,016 A | 3/1989 | Schulte et al. | |
| 5,224,843 A * | 7/1993 | van Lintel | F04B 43/046 417/413.2 |
| 5,620,420 A | 4/1997 | Kriesel | |

(Continued)

FOREIGN PATENT DOCUMENTS

| | | |
|---|---|---|
| CA | 1137374 A | 12/1982 |
| DE | 102007024801 A1 | 11/2008 |

(Continued)

*Primary Examiner* — William R Carpenter
(74) *Attorney, Agent, or Firm* — Dickinson Wright PLLC

(57) ABSTRACT

A medicament delivery device comprising a housing connected to a base and enclosing an interior, the interior having a fluid channel wherein the fluid channel passes from a first position in the interior, to a second position outside the interior, and to a third position in the interior.

18 Claims, 12 Drawing Sheets

(56) References Cited

U.S. PATENT DOCUMENTS

| | | |
|---|---|---|
| 5,693,018 A | 12/1997 | Kriesel et al. |
| 5,707,361 A | 1/1998 | Slettenmark |
| 5,957,895 A | 9/1999 | Sage et al. |
| 6,186,982 B1 | 2/2001 | Gross et al. |
| 6,652,510 B2 | 11/2003 | Lord et al. |
| 6,703,714 B2 | 3/2004 | Mijers |
| 6,981,967 B2 | 1/2006 | Massengale et al. |
| 7,174,923 B2 | 2/2007 | Schom et al. |
| 7,637,897 B2 | 12/2009 | Ginggen |
| 7,713,262 B2 | 5/2010 | Adams et al. |
| 7,815,609 B2 | 10/2010 | Hines et al. |
| 7,938,801 B2 | 5/2011 | Hawkins et al. |
| 8,231,608 B2 | 7/2012 | Pang et al. |
| 8,298,183 B2 | 10/2012 | Menot et al. |
| 8,512,287 B2 | 8/2013 | Cindrich et al. |
| 8,540,172 B2 | 9/2013 | Waterman et al. |
| 8,547,239 B2 | 10/2013 | Peatfield et al. |
| 8,603,051 B2 | 12/2013 | Kuo et al. |
| 8,734,395 B2 | 5/2014 | McAllister |
| D706,415 S | 6/2014 | Levesque et al. |
| 8,821,443 B2 | 9/2014 | Levesque et al. |
| 8,870,829 B2 | 10/2014 | Halili et al. |
| 8,992,478 B2 | 3/2015 | Levesque |
| 9,115,875 B2 | 10/2015 | McAllister |
| 9,173,993 B2 | 11/2015 | Yodfat et al. |
| 9,375,529 B2 | 6/2016 | Searle et al. |
| 9,376,224 B2 | 6/2016 | Gonnelli et al. |
| 9,381,299 B2 | 7/2016 | Kuo et al. |
| 9,415,198 B2 | 8/2016 | McAllister |
| 9,511,187 B2 | 12/2016 | Gonnelli et al. |
| 9,636,451 B2 | 5/2017 | Gonnelli et al. |
| 9,687,599 B2 | 6/2017 | Gonnelli et al. |
| 9,795,735 B2 | 10/2017 | Levesque et al. |
| 9,814,831 B2 | 11/2017 | Gonnelli |
| 9,833,383 B2 | 12/2017 | Gonnelli et al. |
| 9,968,731 B2 | 5/2018 | Gonnelli et al. |
| 9,981,083 B2 | 5/2018 | Gonnelli et al. |
| 2002/0040208 A1 | 4/2002 | Flaherty et al. |
| 2004/0116905 A1* | 6/2004 | Pedersen ........... A61M 5/16877 604/890.1 |
| 2008/0015494 A1 | 1/2008 | Santini |
| 2008/0051698 A1 | 2/2008 | Mounce |
| 2009/0062768 A1* | 3/2009 | Saul ................... A61M 5/16877 604/506 |
| 2009/0062788 A1 | 3/2009 | Saul |
| 2010/0016791 A1 | 1/2010 | Chong et al. |
| 2010/0049123 A1 | 2/2010 | McKenzie et al. |
| 2010/0069891 A1 | 3/2010 | Ginggen |
| 2010/0145276 A1 | 6/2010 | Yodfat |
| 2010/0168710 A1* | 7/2010 | Braithwaite ...... A61M 15/0043 604/403 |
| 2010/0087778 A1 | 10/2010 | Genosar |
| 2010/0274168 A1 | 10/2010 | Gronau et al. |
| 2012/0101451 A1 | 4/2012 | Boit |
| 2012/0156097 A1* | 6/2012 | Beden ..................... A61M 1/16 422/44 |
| 2015/0032051 A1 | 1/2015 | Brandt et al. |
| 2016/0038672 A1 | 2/2016 | Brandt et al. |
| 2016/0184515 A1 | 6/2016 | Shih et al. |
| 2016/0184517 A1 | 6/2016 | Baek et al. |
| 2016/0206815 A1 | 7/2016 | Chong |
| 2018/0036475 A1 | 2/2018 | Lin |

FOREIGN PATENT DOCUMENTS

| | | |
|---|---|---|
| EP | 1 397 946 A1 | 3/2004 |
| EP | 2719412 A1 | 4/2014 |
| JP | 3-39167 A | 2/1991 |
| JP | 2009509697 | 3/2009 |
| JP | 2013-070863 A | 4/2013 |
| JP | 2014-145329 A | 8/2014 |
| WO | 02080637 A1 | 10/2002 |
| WO | 2007038841 | 4/2007 |
| WO | 2009126653 A1 | 10/2009 |

* cited by examiner

PLATE WITH INTEGRAL FLUID PATH CHANNELS

RELATED APPLICATIONS

This application is a division of U.S. Nonprovisional application Ser. No. 15/509,926, filed Mar. 9, 2017, which is a U.S. national stage application under 35 U.S.C. § 371 of International Application No. PCT/US2015/051188, filed Sep. 21, 2015, which claims the benefit under 35 U.S.C. § 119(e) of U.S. Provisional Patent Application Ser. No. 62/053,674, filed on Sep. 22, 2014, the entire disclosures of all of said prior applications being hereby incorporated herein by reference.

FIELD OF THE INVENTION

The present invention relates to medical devices, and more particularly, to medical devices with fluid channels to deliver medicament to a patient.

BACKGROUND OF THE INVENTION

Diabetes is a group of diseases characterized by high levels of blood glucose resulting from the inability of diabetic patients to maintain proper levels of insulin production when required. Diabetes can be dangerous to the affected patient if it is not treated, and it can lead to serious health complications and premature death. However, such complications can be minimized by utilizing one or more treatment options to help control the diabetes and reduce the risk of complications.

The treatment options for diabetic patients include specialized diets, oral medications and/or insulin therapy. The main goal of diabetes treatment is to control the diabetic patient's blood glucose or sugar level. However, maintaining proper diabetes management may be complicated because it has to be balanced with the activities of the diabetic patient. Type 1 diabetes (T1D) patients are required to take insulin (e.g., via injections or infusion) to move glucose from the bloodstream because their bodies generally cannot produce insulin. Type 2 diabetes (T2D) patients generally can produce insulin but their bodies cannot use the insulin properly to maintain blood glucose levels within medically acceptable ranges. In contrast to people with T1D, the majority of those with T2D usually do not require daily doses of insulin to survive. Many people are able to manage their condition through a healthy diet and increased physical activity or oral medication. However, if they are unable to regulate their blood glucose levels, they will be prescribed insulin. For example, there are an estimated 6.2 million Type 2 diabetes patients (e.g., in the United States, Western Europe and Canada) taking multiple-daily-injections (MDI) which consist of a 24-hour basal insulin and a short acting rapid insulin that is taken at mealtimes for glycemic management control.

For the treatment of Type 1 diabetes (T1D) and sometimes Type 2 diabetes (T2D), there are two principal methods of daily insulin therapy. In the first method, diabetic patients use syringes or insulin pens to self-inject insulin when needed. This method requires a needle stick for each injection, and the diabetic patient may require three to four injections daily. The syringes and insulin pens that are used to inject insulin are relatively simple to use and cost effective.

Another effective method for insulin therapy and managing diabetes is infusion therapy or infusion pump therapy in which an insulin pump is used. The insulin pump can provide continuous infusion of insulin to a diabetic patient at varying rates to more closely match the functions and behavior of a properly operating pancreas of a non-diabetic person that produces the required insulin, and the insulin pump can help the diabetic patient maintain his/her blood glucose level within target ranges based on the diabetic patient's individual needs. Infusion pump therapy requires an infusion cannula, typically in the form of an infusion needle or a flexible catheter, that pierces the diabetic patient's skin and through which infusion of insulin takes place. Infusion pump therapy offers the advantages of continuous infusion of insulin, precision dosing, and programmable delivery schedules.

In infusion therapy, insulin doses are typically administered at a basal rate and in a bolus dose. When insulin is administered at a basal rate, insulin is delivered continuously over 24 hours to maintain the diabetic patient's blood glucose levels in a consistent range between meals and rest, typically at nighttime. Insulin pumps may also be capable of programming the basal rate of insulin to vary according to the different times of the day and night. In contrast, a bolus dose is typically administered when a diabetic patient consumes a meal, and generally provides a single additional insulin injection to balance the consumed carbohydrates. Insulin pumps may be configured to enable the diabetic patient to program the volume of the bolus dose in accordance with the size or type of the meal that is consumed by the diabetic patient. In addition, insulin pumps may also be configured to enable the diabetic patient to infuse a correctional or supplemental bolus dose of insulin to compensate for a low blood glucose level at the time when the diabetic patient is calculating the bolus dose for a particular meal that is to be consumed.

Insulin pumps advantageously deliver insulin over time rather than in single injections, typically resulting in less variation within the blood glucose range that is recommended. In addition, insulin pumps may reduce the number of needle sticks which the diabetic patient must endure, and improve diabetes management to enhance the diabetic patient's quality of life. For example, many of the T2D patients who are prescribed insulin therapy can be expected to convert from injections to infusion therapy due to an unmet clinical need for improved control. That is, a significant number of the T2D patients who take multiple-daily-injections (MDI) are not achieving target glucose control or not adhering sufficiently to their prescribed insulin therapy.

Typically, regardless of whether a diabetic patient uses multiple direct injections (MDIs) or a pump, the diabetic patient takes fasting blood glucose medication (FBGM) upon awakening from sleep, and also tests for glucose in the blood during or after each meal to determine whether a correction dose is required. In addition, the diabetic patient may test for glucose in the blood prior to sleeping to determine whether a correction dose is required, for instance, after eating a snack before sleeping.

To facilitate infusion therapy, there are generally two types of insulin pumps, namely, conventional pumps and patch pumps. Conventional pumps use a disposable component, typically referred to as an infusion set, tubing set or pump set, which conveys the insulin from a reservoir within the pump into the skin of the user. The infusion set includes a pump connector, a length of tubing, and a hub or base from which a cannula, in the form of a hollow metal infusion needle or flexible plastic catheter, extends. The base typically has an adhesive that retains the base on the skin surface during use. The cannula can be inserted onto the skin manually or with the aid of a manual or automatic insertion device. The insertion device may be a separate unit employed by the user.

Another type of insulin pump is a patch pump. Unlike a conventional infusion pump and infusion set combination, a patch pump is an integrated device that combines most or all of the fluidic components in a single housing. Generally, the housing is adhesively attached to an infusion site on the patient's skin, and does not require the use of a separate infusion or tubing set. A patch pump containing insulin adheres to the skin and delivers the insulin over a period of time via an integrated subcutaneous cannula. Some patch pumps may wirelessly communicate with a separate controller device (as in one device sold by Insulet Corporation under the brand name OmniPod®), while others are completely self-contained. Such patch pumps are replaced on a frequent basis, such as every three days, or when the insulin reservoir is exhausted. Otherwise, complications may occur, such as restriction in the cannula or the infusion site.

As patch pumps are designed to be a self-contained unit that is worn by the patient, preferably, the patch pump is small, so that it does not interfere with the activities of the user. Thus, to minimize discomfort to the user, it would be preferable to minimize the overall thickness of the patch pump. However, to minimize the thickness of the patch pump, the size of its constituent parts should be reduced as much as possible.

In current patch pump designs, tubes, such as plastic tubes, are employed as fluid pathways to route fluid flow from one internal component to another. For example, a tube can connect a medicament reservoir with a delivery needle, but the space required to internally house such a tube adds to the overall size of the patch pump. The use of tubes can increase cost and can result in additional complexity during automated device assembly processes. For example, such device assembly includes connecting the tubes, which adds steps to the assembly process. In addition, preventing leaks from such connections can give rise to additional challenges.

Accordingly, a need exists for an improved fluid path design for use in a limited space environment, such as in a patch pump device, which can cost-effectively transport medicament, while minimizing or reducing the overall size and complexity of the device.

SUMMARY OF EMBODIMENTS OF THE INVENTION

It is an aspect of the present invention to provide a patch pump in which one or more fluid channels bypass a fluid ingress barrier to effectively and efficiently administer the medicament to the patient. Sensors and fluid channels provide a bypass from a wet interface to a dry interface with minimal complexity by routing flow away from the specific interface.

The foregoing and/or other aspects of the present invention can be achieved by providing a device for delivering medicament into skin of a patient, the device having a housing, which includes a reservoir for housing the medicament, a first internal region that is sealed from fluid ingress and includes one or more components, and a second internal region that is not sealed from fluid ingress and includes one or more components. The housing also has a barrier that separates the first internal region and the second internal region, a delivery cannula that delivers the medicament into the skin of the patient, and a base including a bottom surface for orienting toward the skin of the patient. The bottom surface of the base has one or more fluid channels disposed therein and at least one of the fluid channels is in fluid communication with the delivery cannula.

The foregoing and/or other aspects of the present invention can also be achieved by providing a medicament delivery device including a housing having an interior, the housing having a fluid channel disposed therein. The fluid channel passes from a first position in the interior, to a second position outside the housing, and to a third position in the interior.

The foregoing and/or other aspects of the present invention can be further achieved by providing a medicament delivery method including disposing medicament in an interior of a housing and transporting the medicament in a fluid channel traveling from the interior of the housing to outside of the housing, and back into the interior of the housing.

Moreover, the foregoing and/or other aspects of the present invention can be achieved by providing a medicament delivery device including a housing having an interior, the housing including a reservoir for housing medicament, a fill port in fluid communication with the reservoir, a delivery mechanism that delivers the medicament into skin of a patient, a pump that controls flow of the medicament to the delivery mechanism, and a base having first and second fluid channels disposed therein. The pump is in fluid communication with the delivery mechanism via the first fluid channel and one of the fluid channels is disposed, at least in part, outside the interior of the housing.

Additional and/or other aspects and advantages of the present invention will be set forth in the description that follows, or will be apparent from the description, or may be learned by practice of the invention. The present invention may comprise delivery devices and methods for forming and operating same having one or more of the above aspects, and/or one or more of the features and combinations thereof. The present invention may comprise one or more of the features and/or combinations of the above aspects as recited, for example, in the attached claims.

BRIEF DESCRIPTION OF THE DRAWINGS

The above and/or other aspects and advantages of embodiments of the invention will be more readily appreciated from the following detailed description, taken in conjunction with the accompanying drawings, of which.

DETAILED DESCRIPTION OF EMBODIMENTS OF THE PRESENT INVENTION

Figure 1:
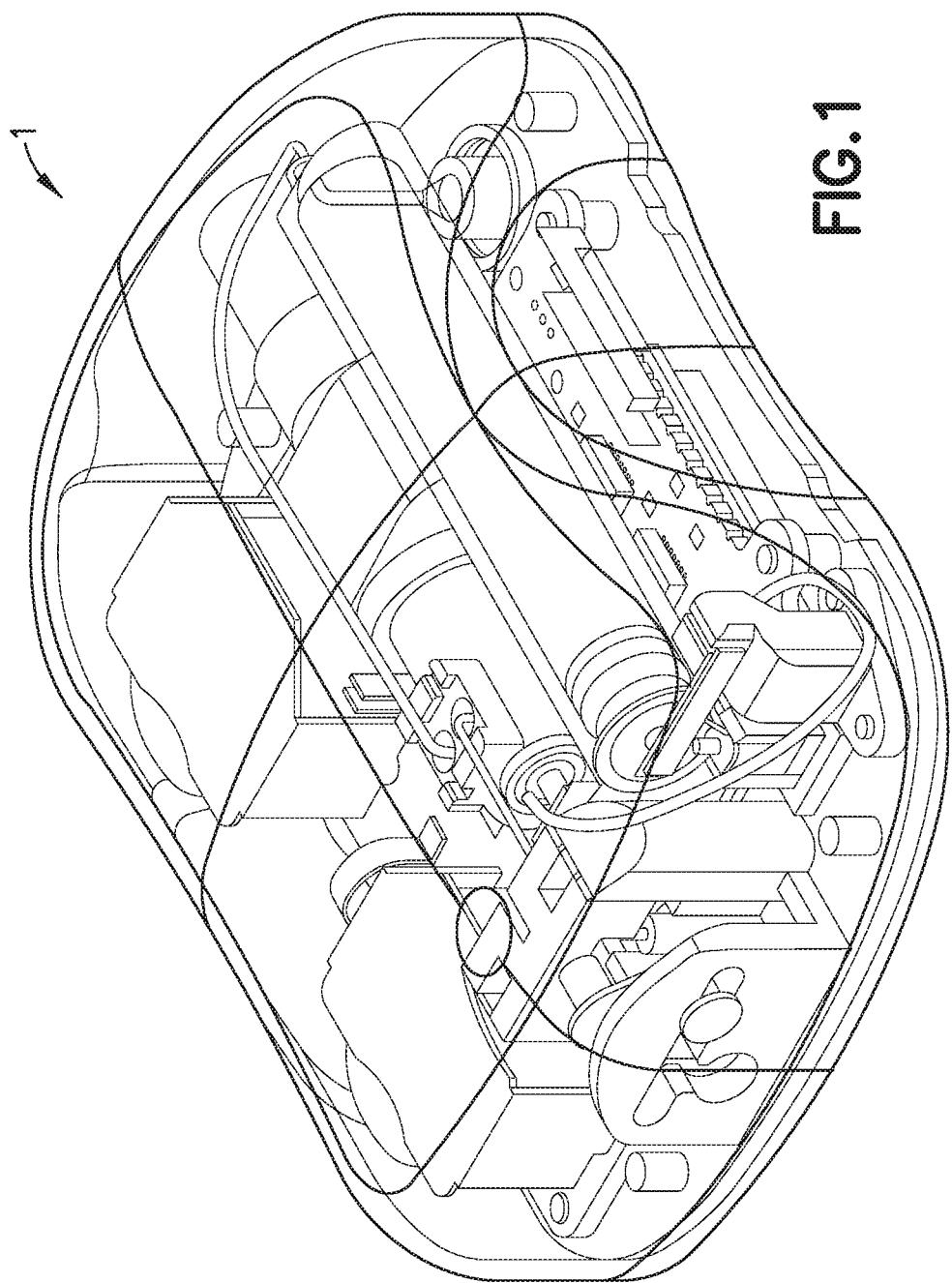
FIG. 1 is a perspective view of a patch pump constructed in accordance with an illustrative embodiment of the present invention.

Reference will now be made in detail to embodiments of the present invention, which are illustrated in the accompanying drawings, wherein like reference numerals refer to like elements throughout. The embodiments described herein exemplify, but do not limit, the present invention by referring to the drawings.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

The illustrative embodiments are described with reference to diabetes management using insulin therapy. It is to be understood that these illustrative embodiments can be used with different drug therapies and regimens to treat other physiological conditions than diabetes using different medicaments than insulin.

Figure 2:
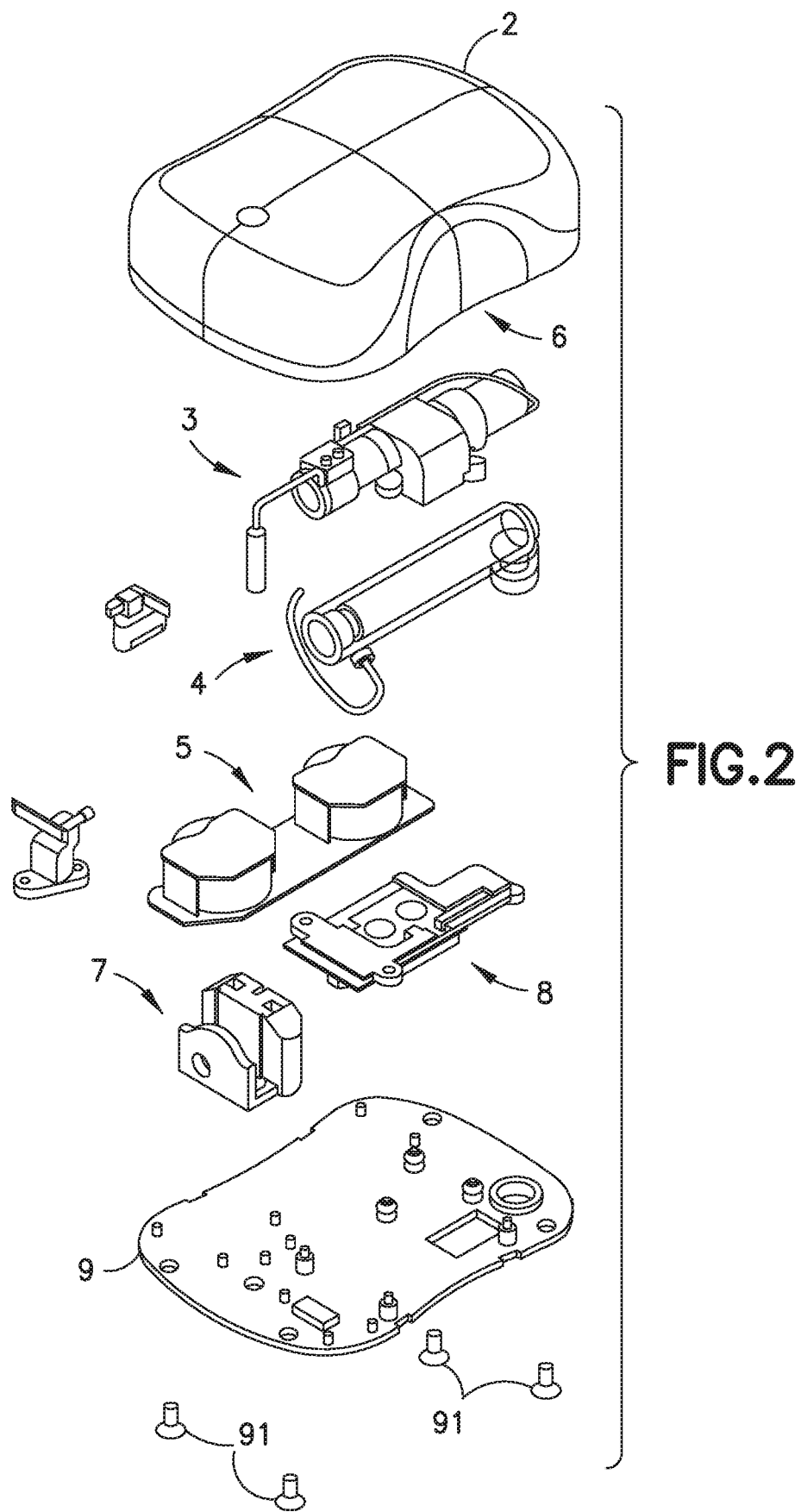
FIG. 2 is an exploded view of the various components of the patch pump of FIG. 1, illustrated with a cover.

FIG. 1 is a perspective view of an exemplary embodiment of a medicine delivery device comprising a patch pump 1 according to an exemplary embodiment of the invention. The patch pump 1 is illustrated with a see-through cover for clarity and illustrates various components that are assembled to form the patch pump 1. FIG. 2 is an exploded view of the various components of the patch pump of FIG. 1, illustrated with a main cover 2. The various components of the patch pump 1 may include: a reservoir 4 for storing insulin; a pump 3 for pumping insulin out of the reservoir 4; a power source 5 in the form of one or more batteries; an insertion mechanism 7 for inserting an inserter needle with a catheter into a user's skin; control electronics 8 in the form of a circuit board with optional communications capabilities to outside devices such as a remote controller and computer, including a smart phone; a pair of dose buttons 6 on the cover 2 for actuating an insulin dose, including a bolus dose; and a base 9 to which various components above may be attached via fasteners 91. The patch pump 1 also includes various fluid connector lines that transfer insulin pumped out of the reservoir 4 to the infusion site.

Figure 3:
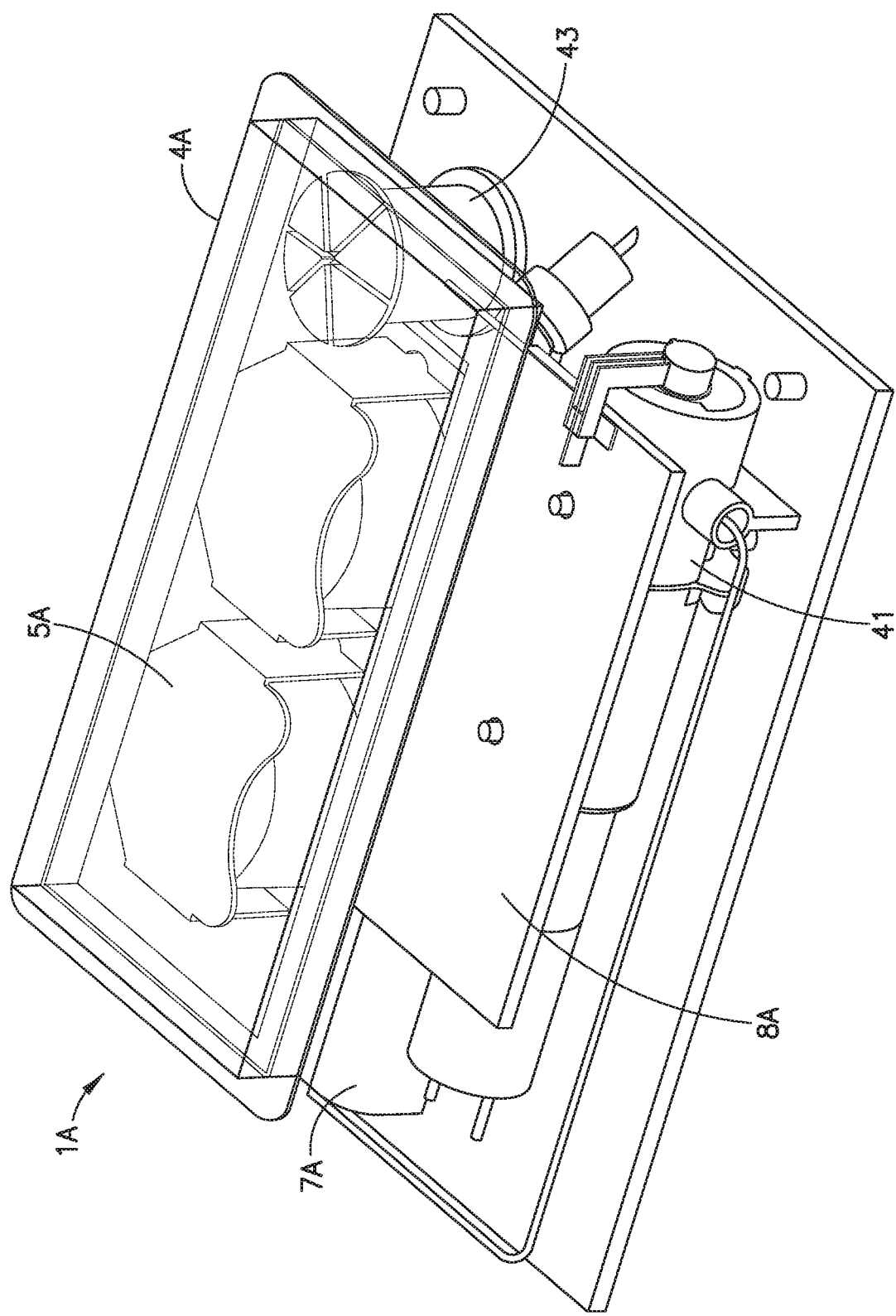
FIG. 3 is a perspective view of an alternative design for a patch pump having a flexible reservoir, illustrated without a cover, in accordance with an illustrative embodiment of the present invention.

FIG. 3 is a perspective view of an alternative design for a patch pump 1A having a flexible reservoir 4A, and illustrated without a cover. Such arrangement may further reduce the external dimensions of the patch pump 1A, with the flexible reservoir 4A filling voids within the patch pump 1A. The patch pump 1A is illustrated with a conventional cannula insertion device 7A that inserts the cannula, typically at an acute angle, less than 90 degrees, at the surface of a user's skin. The patch pump 1A further comprises: a power source 5A in the form of batteries; a metering sub-system 41 that monitors the volume of insulin and includes a low volume detecting ability; control electronics 8A for controlling the components of the device; and a reservoir fill port 43 for receiving a refill syringe 45 to fill the reservoir 4A.

Figure 4:
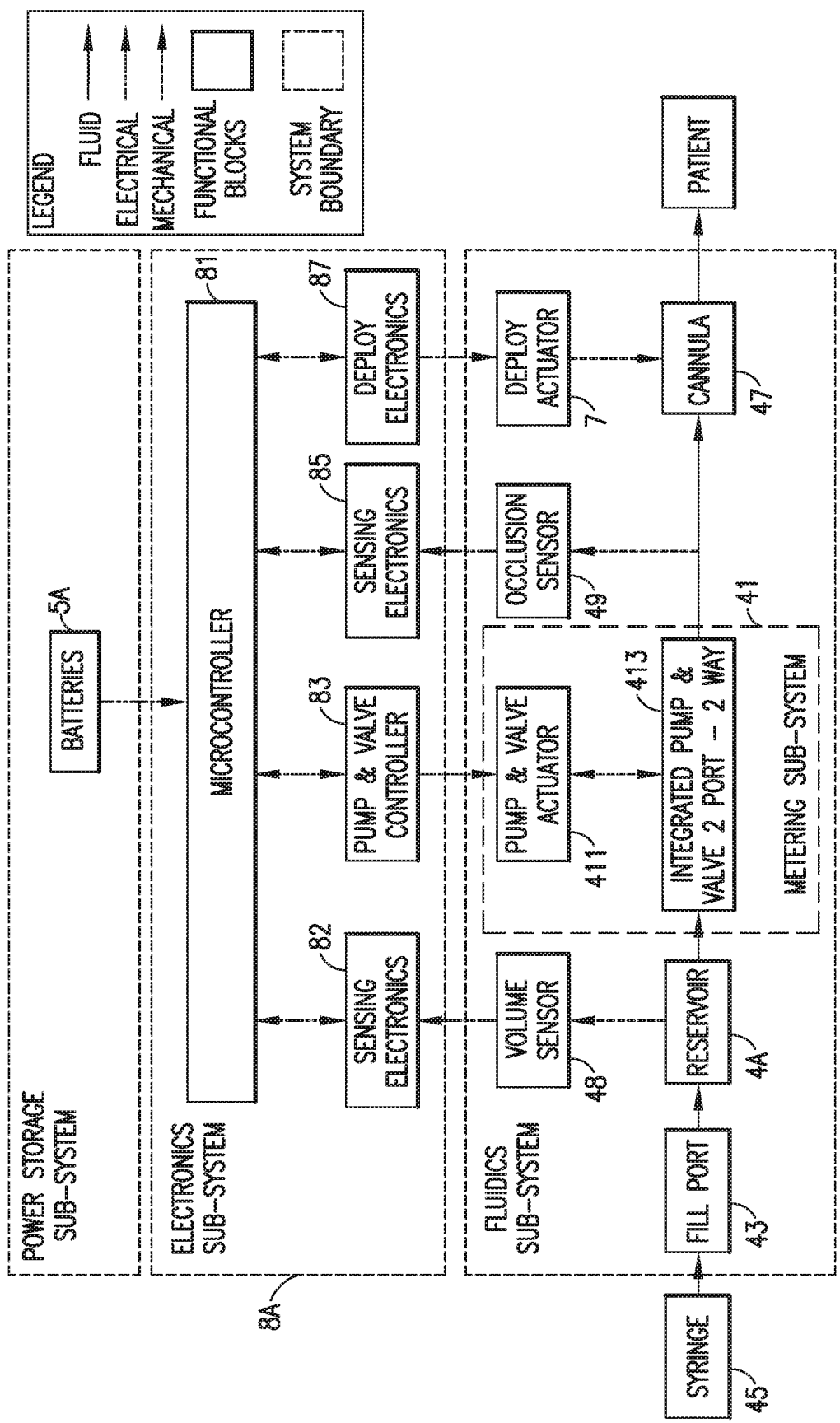
FIG. 4 is a perspective view of a patch-pump fluidic architecture and metering sub-system diagram of the patch pump of FIG. 3.

FIG. 4 is a patch-pump fluidic architecture and metering sub-system diagram of the patch pump 1A of FIG. 3. The power storage sub-system for the patch pump 1A includes batteries 5A. The control electronics 8A of the patch pump 1A may include a microcontroller 81, sensing electronics 82, pump and valve controller 83, sensing electronics 85, and deployment electronics 87, which control the actuation of the patch pump 1A. The patch pump 1A includes a fluidics sub-system that may include a reservoir 4A, volume sensor 48 for the reservoir 4A, a reservoir fill port 43 for receiving a refill syringe 45 to refill the reservoir 4A. The fluidics sub-system may include a metering system comprising a pump and valve actuator 411 and an integrated pump and valve mechanism 413. The fluidics sub-system may further include an occlusion sensor, a deploy actuator, as well as the cannula 47 for insertion into an infusion site on the user's skin. The architecture for the patch pumps of FIGS. 1 and 2 is the same or similar to that which is illustrated in FIG. 4.

Figure 5:
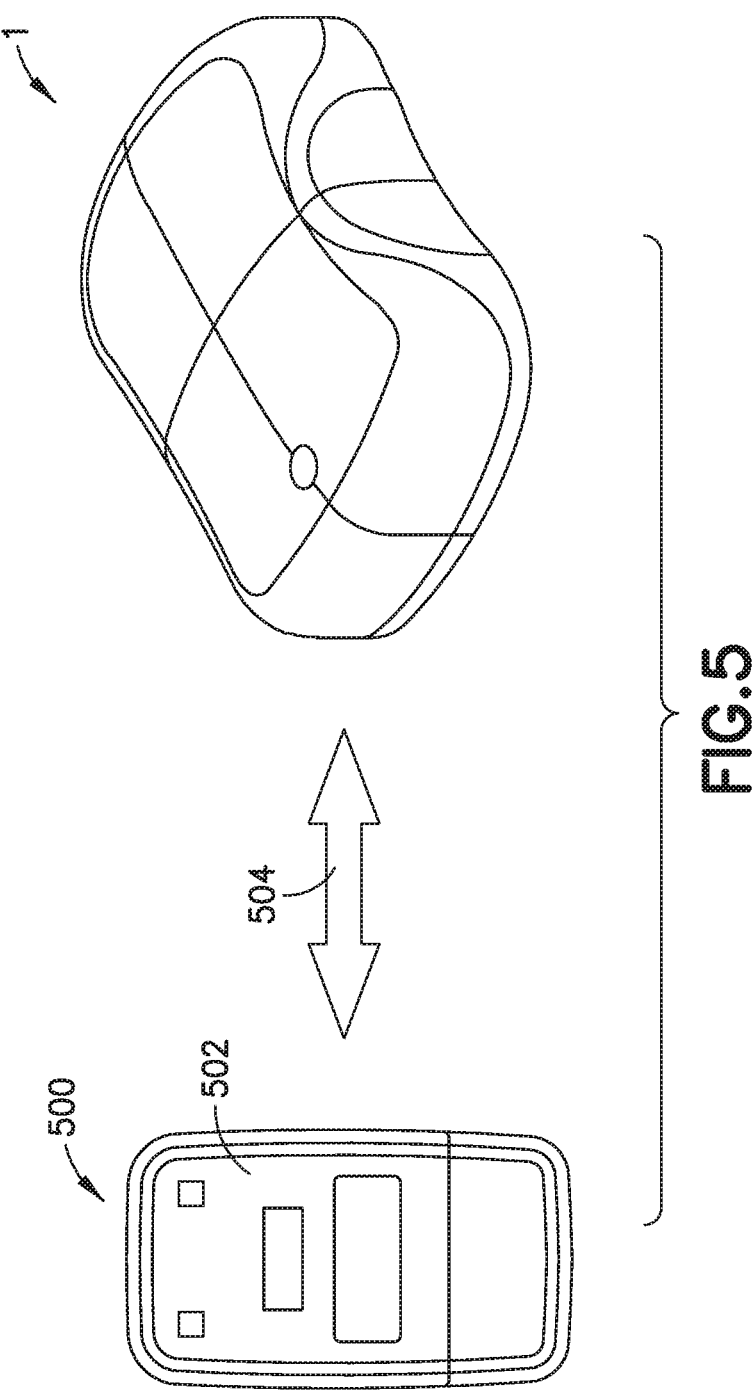
FIG. 5 illustrates an example wireless remote controller for controlling the operation of a medicine delivery device such as, for example, a patch pump, in accordance with an illustrative embodiment of the present invention.

With reference to FIG. 5, the wearable medical delivery device (e.g., insulin delivery device (IDD) such as patch pump 1 is operable in conjunction with a remote controller that preferably communicates wirelessly with the pump 1 and is hereinafter referred to as the wireless controller (WC) 500. The WC can comprise a graphical user interface (GUI) display 502 for providing a user visual information about the operation of the patch pump 1 such as, for example, configuration settings, an indication when a wireless connection to the patch pump is successful, and a visual indication when a dose is being delivered, among other display operations. The GUI display 502 can include a touchscreen display that is programmed to allow a user to provide touch inputs such as a swipe to unlock, swipe to confirm a request to deliver a bolus, and selection of confirmation or settings buttons, among other user interface operations.

The WC 500 can communicate with the delivery device (e.g., patch pump 1) using any one or more of a number of communication interfaces 504. For example, a near field radiation interface is provided to synchronize the timing of the WC and patch pump 1 to facilitate pairing upon start up. Another interface can be provided for wireless communication between the WC and the patch pump 1 that employs a standard BlueTooth Low Energy (BLE) layer, as well as Transport and Application layers. Non-limiting examples of Application layer commands include priming, delivering basal dose, delivering bolus dose, cancelling insulin delivery, checking patch pump 1 status, deactivating the patch pump 1, and patch pump 1 status or information reply.

Figure 6:
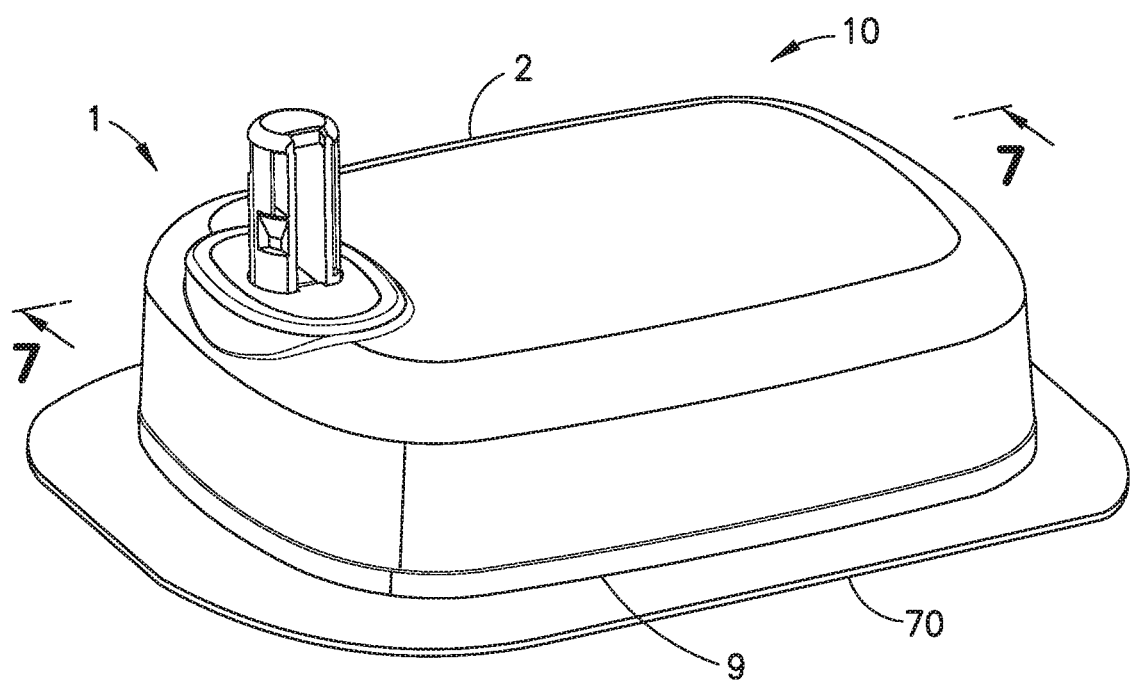
FIG. 6 is a perspective view of a patch pump in accordance with an illustrative embodiment of the present invention.

FIG. 6 is a perspective view of a patch pump 1 according to an exemplary embodiment of the present invention. The patch pump 1 has a housing 10, which includes a main cover 2 liquid sealed or, preferably, hermetically sealed to a base 9. The base 9 carries various components as described below in detail. The hermetic seal prevents fluid ingress and prevents other particles from passing the seal. Embodiments of the patch pump 1 also include a vent or a vent membrane along with a sealing method described herein to provide pressure equalization.

Embodiments of the seal include, for example, a liquid-tight seal, an O-ring seal or another mechanical seal, a gasket, an elastomer, a heat seal, an ultra-sonically welded seal, a laser weld, chemical joining, an adhesive, a solvent weld, or an adhesive weld. Laser welding is the preferred sealing method because, when laser welding is properly performed, a seamless fully hermetic seal is formed. The vent or the vent membrane continues to have the functional purpose of equalizing internal pressure and providing a sterile environment. One skilled in the art will appreciate that other seals can be used without departing from the scope of the present invention.

Figure 7:
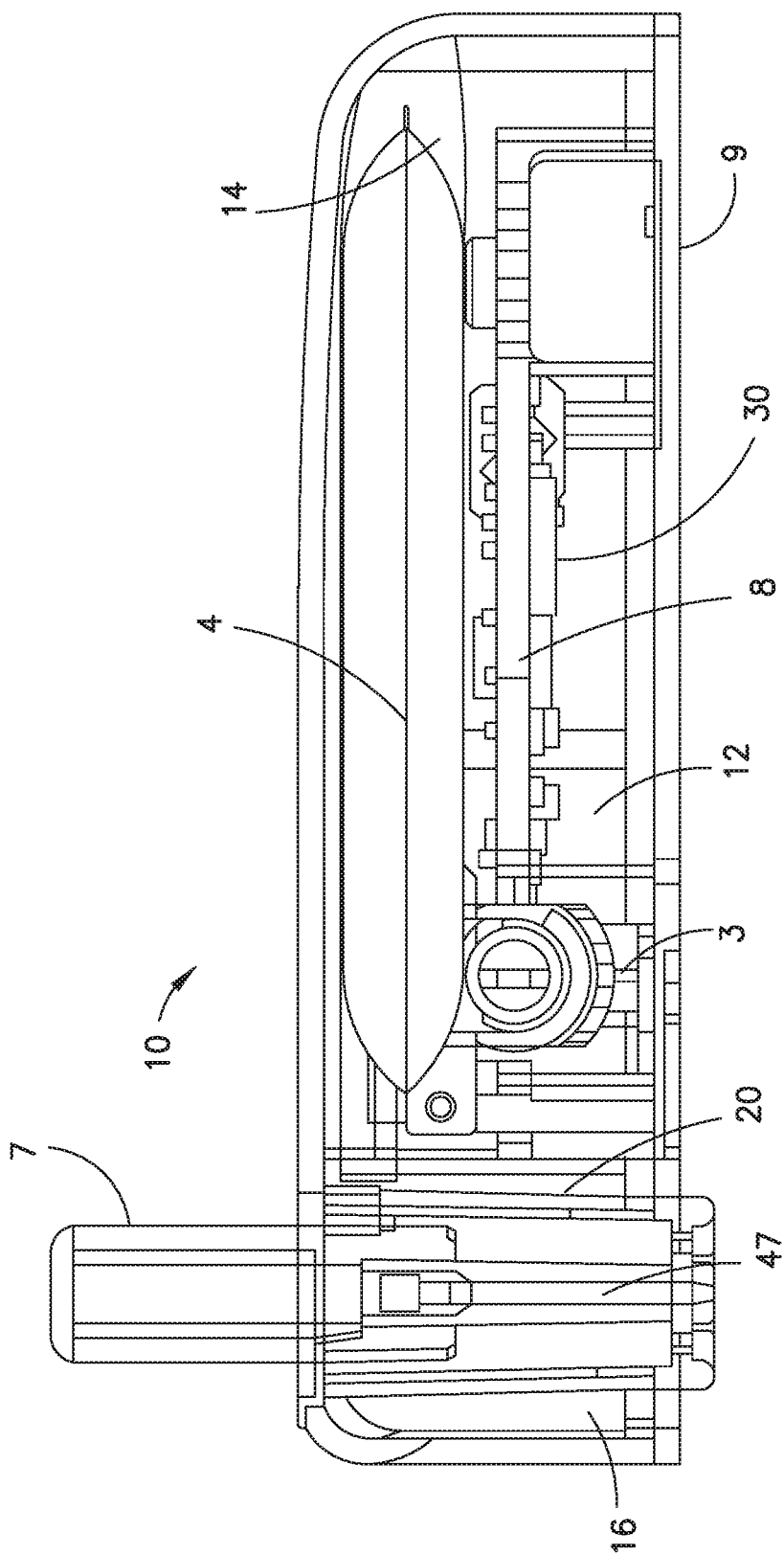
FIG. 7 is a cross-sectional view of FIG. 6 taken along line 7-7 of FIG. 6.

FIG. 7 is a cross-sectional view of the patch pump 1 illustrating various components. The main cover 2 and the base 9 define an interior 12 divided by a barrier 20 into a first internal region 14 and a second internal region 16. According to one embodiment, the patch pump 1 preferably includes a reservoir 4 for storing medicament (such as insulin), a pump 3 for pumping the medicament to exit the reservoir 4, and a force sensing resistor 30 for detecting an amount of pressure in a medicament flow path. The patch pump 1 also preferably includes electronics 8 for programming and operating the patch pump 1, and an insertion mechanism 7 for inserting a cannula 47 into a skin of the patient to deliver medicament.

As previously noted, the interior 12 of the patch pump 1 is divided by the barrier 20 into the first internal region 14 and the second internal region 16. According to one embodiment, the barrier 20 is a part of the main cover 2. Preferably, the barrier 20 is integrally formed as a unitary structure with the main cover 2. The barrier 20 is preferably sealed to a protrusion 18 on the base 9 such that the interface between the barrier 20 and the protrusion 18 is hermetically joined using any of the processing methods described above or any other appropriate conventional sealing method. Alternatively, the interface between the barrier 20 and the protrusion 18 can be liquid sealed. The barrier 20 separates the first internal region 14 from the second internal region 16 and protects the first internal region 14 from fluid ingress. According to one embodiment, the second internal region 16 is not sealed from fluid ingress.

The first internal region 14 includes components such as the pump 3, the force sensing resistor 30, and the electronics 8. Examples of the electronics 8 include semiconductor chips, controllers, diodes, antennas, coils, batteries, discrete components (resistors and capacitors, for example) and circuit boards used to operate and control the patch pump 1 and operate the pump 1 in conjunction with the WC 500. As readily understood by the skilled artisan, it is desirable to have a dry environment for proper operation of these components, particularly the electronics 8. The second internal region 16 includes the insertion mechanism 7 and the cannula 47. According to one embodiment, because the insertion mechanism 7 interfaces with the skin of a patient, the second internal region 16 is neither a hermetically sealed environment, nor a liquid-tight environment.

According to one embodiment, the components of the first internal region 14 are different from the components of the second internal region 16. Alternatively, the first internal region 14 and the second internal region 16 share some of the same components. For example, in some embodiments, portions of the reservoir 4 are disposed in both the first and second internal regions 14, 16. When the reservoir and the insertion mechanism 7 are separated by the barrier 20, however, the two internal regions 14, 16 fluidly communicate for effective operation of the patch pump 1.

Figure 8:
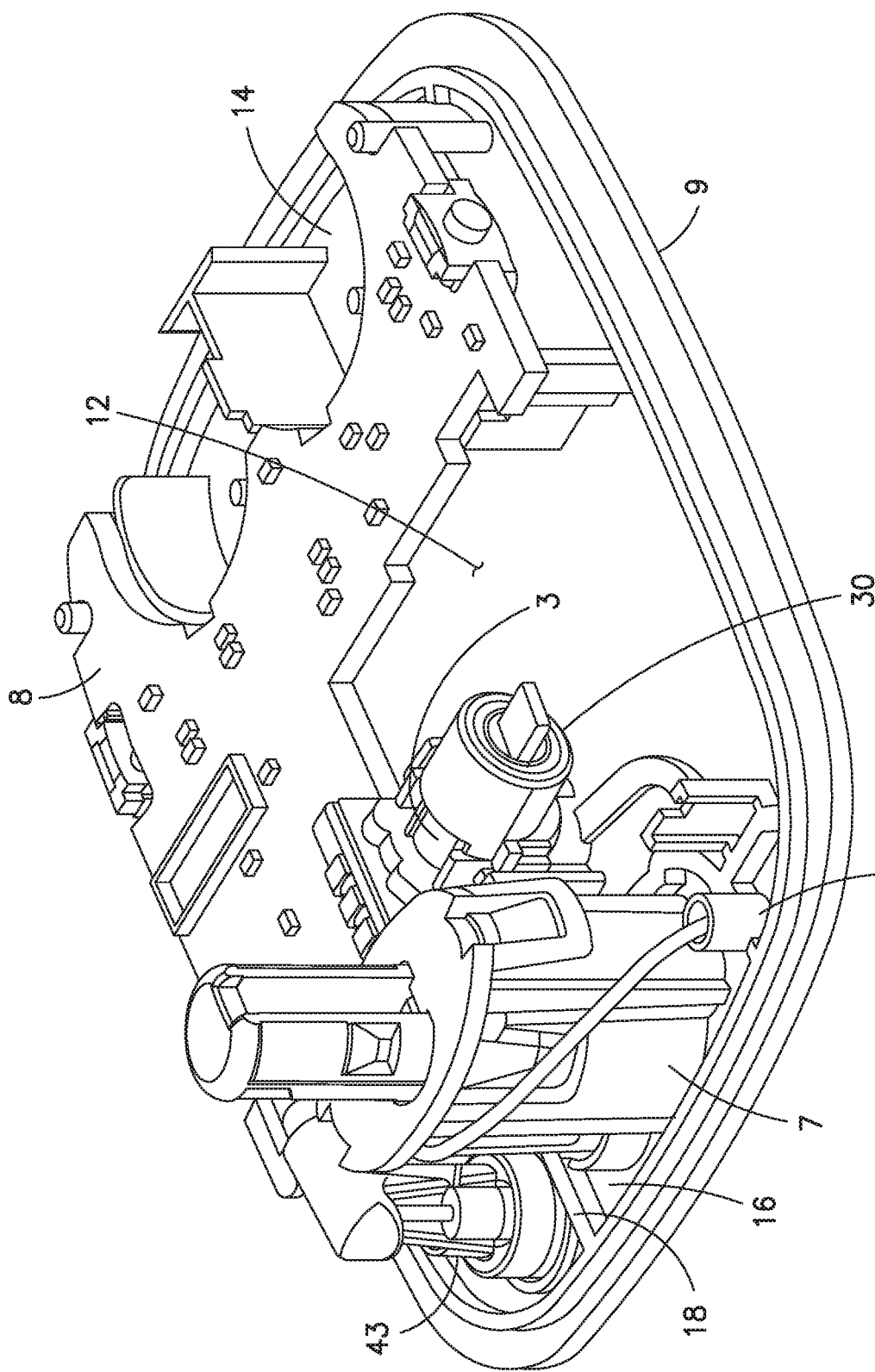
FIG. 8 is a perspective view of the patch pump of FIG. 6, omitting a cover and a reservoir.

FIG. 8 illustrates some of the main components of the patch pump 1 in a perspective view with the main cover 2 and the reservoir 4 removed for clarity. According to one embodiment, a fill port 43 is a conduit for supplying the medicament to the reservoir 4. The fill port 43 can be disposed in the first internal region 14 or the second internal region 16, but is preferably located in the first internal region 14. In some embodiments, the fill port 43 includes a portion that serves as part of the flow path for medicament exiting the reservoir 4.

Preferably, a receptacle 32 is connected to the insertion mechanism 7 by tubing, for example, to transfer the medicament to the insertion mechanism 7 prior to injection into the skin of the patient. According to one embodiment, the receptacle 32 is disposed in the second internal region 16.

Figure 9:
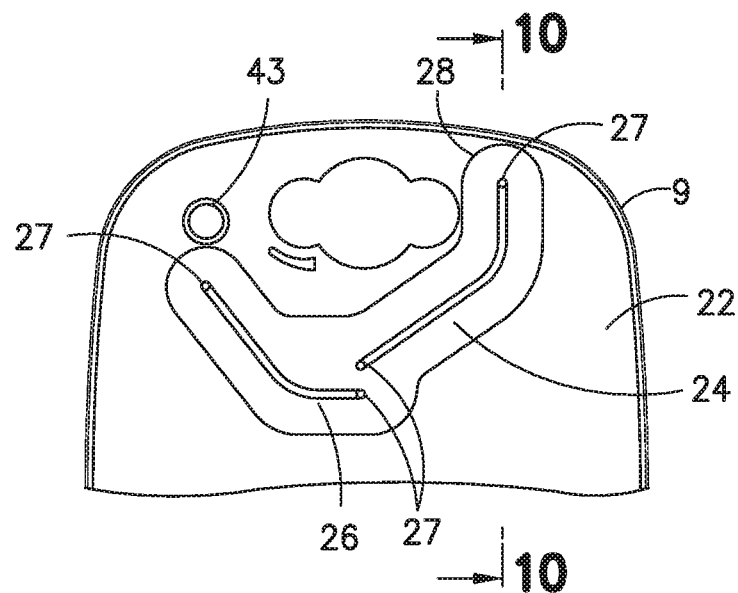
FIG. 9 is a bottom view of the patch pump of FIG. 6.

FIG. 9 illustrates a bottom surface 22 of the base 9 of the patch pump 1. During use, the bottom surface 22 is oriented toward the skin of the patient. In some embodiments, the bottom surface 22 can include adhesive that removably attaches the base 9 to the skin of the patient. Alternatively, an adhesive pad 70, as illustrated in FIG. 6, adheres to both the bottom surface 22 and the skin of the patient. Preferably, 3M™ medical tape (e.g. product no. 1776) is the adhesive used, although various types of known industry adhesives can be used. However, the adhesive is carefully selected to ensure compatibility with human skin to prevent undesired reactions. Also, compatibility of the adhesive and the insulin is considered in case that the adhesive and the insulin accidentally mix. The adhesive or adhesive pad are also placed over a fluid channel cover 28 covering first and second fluid channels 24, 26 which are described in detail below.

As shown in FIG. 9, the bottom surface 22 of the base 9 includes first and second fluid channels 24, 26. The first and second fluid channels 24, 26 provide fluid pathways between various components in the patch pump 1. According to one embodiment, the first and second fluid channels 24, 26 advantageously establish fluid communication between various components such as the reservoir 4, the fill port 43, the force sensing resistor 30, the pump 3, and the insertion mechanism 7.

Preferably, the first and second fluid channels 24, 26 are recessed from (or inscribed into) the bottom surface 22, and are formed through a molding process, such as injection molding, or by a cutting process, such as milling. In other embodiments, the first and second fluid channels 24, 26 are disposed on the main cover 2, or on the base 9 within the interior 12 of the patch pump 1. Similar fluid channels can be positioned in a plurality of locations in embodiments of the device.

The cross-sectional shape of the first and second fluid channels 24, 26 is defined based on desired flow characteristics. The geometry of the first and second flow channels 24, 26 is selected based on factors such as cost, manufacturing capability, and desired use. Exemplary cross-sectional profiles of the first and second fluid channels 24, 26 include square, rectangular, and semi-circular. One skilled in the art will appreciate that other cross-sectional profiles can be employed without departing from the scope of the present invention.

Preferably, the first and second fluid channels 24, 26 are sized to allow unrestricted medicament fluid flow. In other words, the pump 3 connected to the first and second fluid channels 24, 26 controls and determines the medicament fluid flow rate, instead of the size of the first and second fluid channels 24, 26. Specifically, if the first and second fluid channels 24, 26 are too small, capillary action can occur, potentially resulting in the obstruction of medicament fluid flow. Preferably, the cross-sectional area of the first and second fluid channels 24, 26 is greater than the gage of the cannula 47.

According to one embodiment as illustrated in FIG. 9, the first and second fluid channels 24, 26 are encapsulated by a fluid channel cover 28 which is illustrated as being transparent for clarity. But one skilled in the art will appreciate that the opacity of the fluid channel cover 28 or other portions of the device can vary without departing from the scope of the present invention. The fluid channel cover 28 is, for example, clear film, foil, a flexible sheet/film or a semi-rigid/rigid part made of any suitable material.

According on one embodiment, the film channel cover 28 is made of foil available from Oliver-Tolas Healthcare Packaging (e.g., TPC-0777A foil). Preferably, the film channel cover 28 is made of Oliver-Tolas Healthcare Packaging IDT-6187 clear film and is heat sealed or heat staked to the bottom surface 22 of the base 9 to embed the first and second fluid channels 24, 26. Laser welding, for example, applies laser light through the clear film to fix the film channel cover 28 to the bottom surface 22 of the base 9. Laser welding is advantageous because a laser can straddle the channel edge of the fluid channels 24, 26 during the welding process and adhere the film to the base 9 in areas that are closer to the channel edges than other methods.

The fluid channel cover 28 is sealed to the base 9 via any of the processing methods described above. Accordingly, it is desirable for the material of the fluid channel cover 28 to be compatible with the material of the base 9 for the purposes of effective processing, joining, liquid sealing, and hermetic sealing. In addition, because the medicament comes into contact with the fluid channel cover 28, care is taken in the selection of the fluid channel cover 28 to ensure compatibility with the medicament.

The sealed fluid channel cover 28 encloses and protects the medicament from any contamination while travelling through the first and second fluid channels 24, 26. According to one embodiment, a single fluid channel cover 28 encapsulates each of the first and second fluid channels 24, 26. Alternatively, a separate fluid channel cover 28 can encapsulate each of the first and second fluid channels 24, 26. Because fluid channels can also be disposed in the interior 12 of the patch pump 1 as described above, one or more fluid channel covers 28 can be appropriately disposed in the interior 12 of the patch pump 1 as well.

Figure 10:
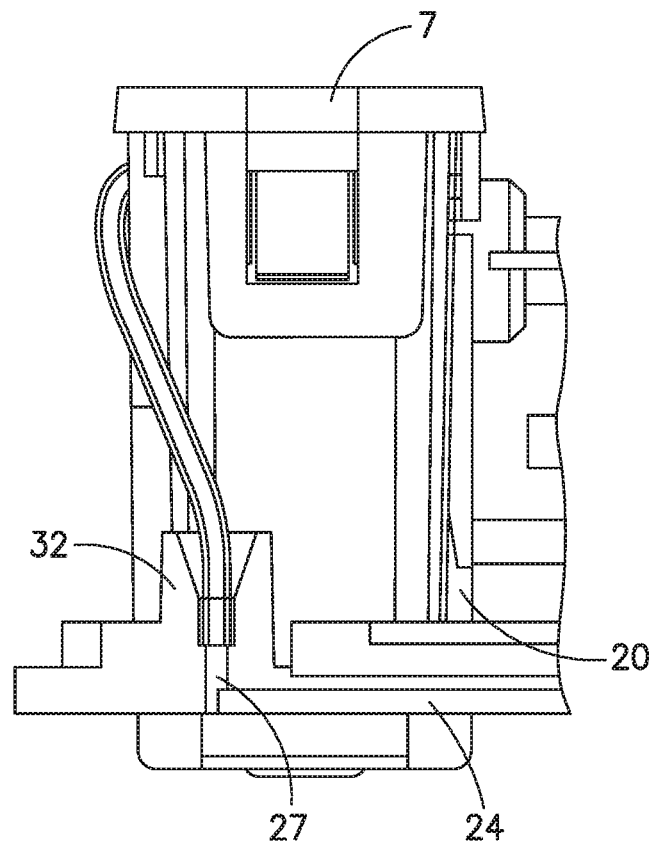
FIG. 10 is a partial cross-sectional view of the patch pump of FIG. 6 taken along line 10-10 of FIG. 9.

FIG. 10 is a partial cross-sectional view of the patch pump 1 of FIG. 6. According to one embodiment, the base 9 includes a fluid channel passageway 27, such as a through hole 27, which extends through the base 9. As shown in FIG. 10, the fluid channel passageway 27 advantageously connects the receptacle 32 to a first end of the first fluid channel 24. According to one embodiment, a fluid channel passageway 27 is similarly present at each end of the first and second fluid channels 24, 26 (see FIG. 9). Preferably, the fluid channel passageway 27 disposed in the base 9 at a second end of the first fluid channel 24 connects directly to the pump 3 disposed in the first internal region 14. Similarly, in a preferred embodiment, opposing ends of the second fluid channel 26 connect the reservoir fill port 43 and the pump 3 via the fluid channel passageways 27.

According to one embodiment, the medicament exits the first internal region 14 of the patch pump 1 via the passageway 27 in the base 9, entering the first fluid channel 24 in the bottom surface 22 outside of the interior 12 of the patch pump 1. Subsequently, via the fluid channel passageway 27 disposed at the first end of the first fluid channel 24, the medicament reenters the interior 12 of the patch pump 1 into the second internal region 16. By routing the medicament through the first fluid channel 24 outside the interior 12 of the patch pump 1, the first fluid channel 24 advantageously and effectively bypasses the barrier 20. Therefore, the first fluid channel establishes fluid communication between the pump 3 and the cannula 47 while bypassing the barrier 20, thereby maintaining the barrier 20 integrity. Thus, the first fluid channel 24 advantageously provides fluid communication between the first internal region 14, which is sealed from fluid ingress, and the second internal region 16, which is not sealed from fluid ingress without compromising the integrity of the barrier 20.

The configuration of the first and second fluid channels 24, 26 in the patch pump 1 provides a plurality of exemplary benefits. Because the first and second fluid channels 24, 26 are integral to the base 9, they are conveniently manufactured through molding and/or milling, thereby potentially reducing manufacturing costs. Additionally, the barrier 20 provides an effective seal between the first and second internal regions 14, 16 because the first and second fluid channels 24, 26 bypass the barrier 20 instead of penetrating the barrier 20. Such a sealing configuration advantageously ensures that the critical components in the first internal region 14 do not fail due to fluid ingress. The critical components are disposed in preferred locations, which provides for optimal component arrangement. Thus, the use of first and second fluid channels 24, 26 outside of the interior 12 of the patch pump 1 provides configurational freedom to designers, aids optimization of the interior space, and aids reduction of the overall size of the patch pump 1.

Figure 11:
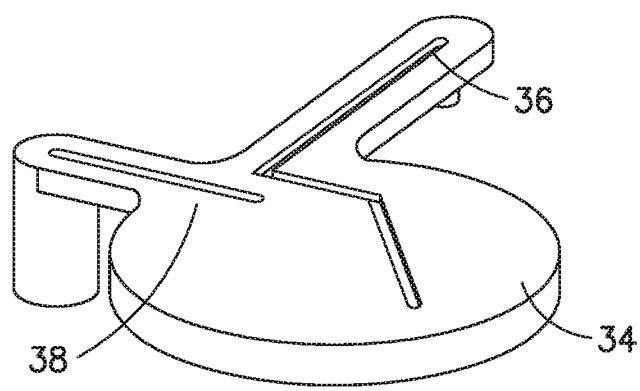
FIG. 11 is a perspective view of a plate in accordance with an embodiment of the present invention.
Figure 12:
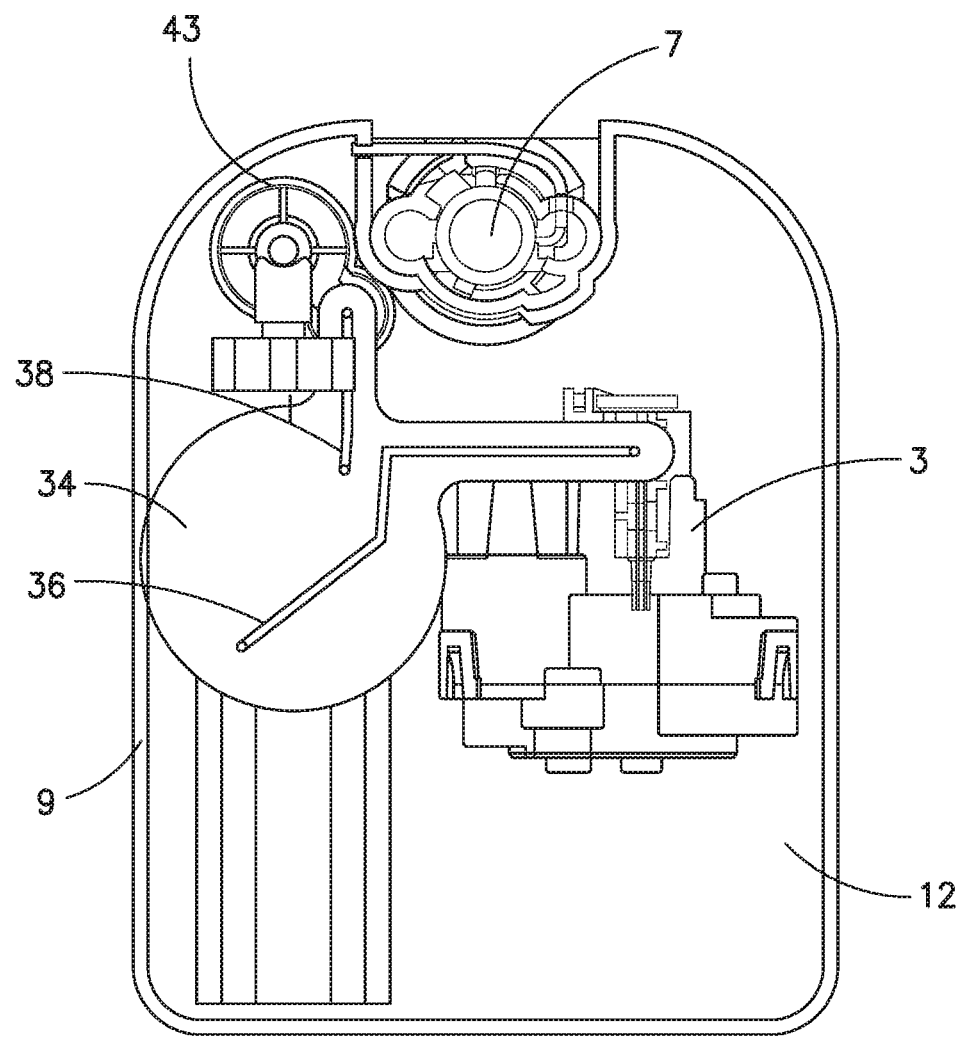
FIG. 12 is a perspective view of a patch pump incorporating the plate of FIG. 11.

In an alternate embodiment, as illustrated in FIGS. 11 and 12, a flow channel plate 34 is disposed in the interior 12 of the patch pump 1 to provide a medicament fluid pathway. The flow channel plate 34 includes first and second plate fluid channels 36, 38, encapsulated by a fluid channel cover 28, which is omitted for clarity. The plate fluid channels 36, 38 route medicament fluid flow to the various components through the interior 12 of the patch pump 1.

According to one embodiment, the force sensing resistor 30 is integrally formed into the flow channel plate 34 for in-line pressure sensing of the medicament fluid flow path. One embodiment of a flow channel plate 34 incorporates a receptacle to replace the fill port 43. Ports, receptacles, or joints can advantageously be included in the flow channel plate 34 to mate various components via a fluid path. According to one embodiment, the flow channel plate 34 is entirely disposed in the first internal region 14.

The medicament flow path in the flow channel plate 34 offers further flexibility and space optimization options for the arrangement of the various components in the patch pump 1. FIG. 12 illustrates an exemplary embodiment in which components at various locations in the patch pump 1 establish fluid communication via the first and second plate fluid channels 36, 38 in the flow channel plate 34. According to one embodiment, the first and second plate fluid channels 36, 38 in the flow channel plate 34 cooperate with the first and second fluid channels 24, 26 in the base 9 to provide fluid communication from the reservoir 4 to the insertion mechanism 7.

Figure 13:
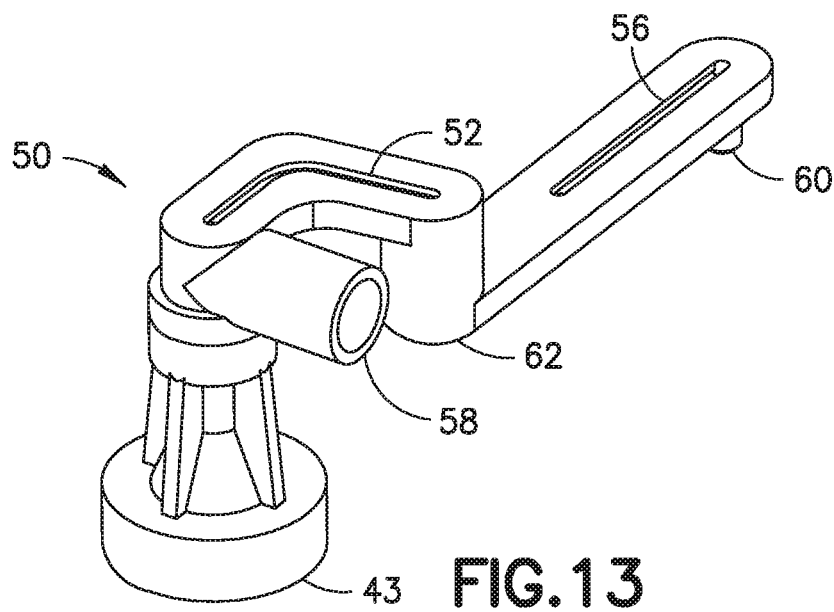
FIGS. 13-15 are perspective views of a flow channel member in accordance with an embodiment of the present invention.
Figure 14:
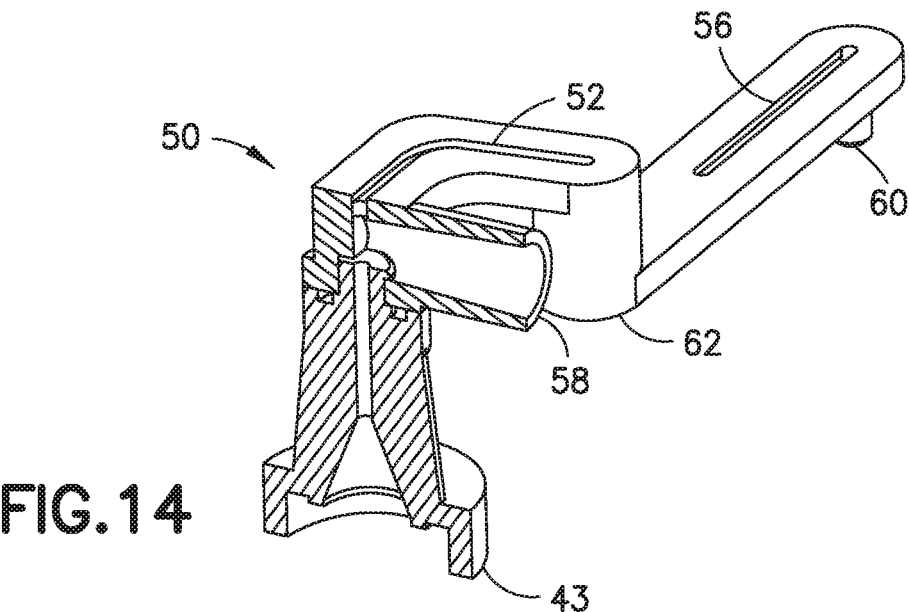
Figure 15:
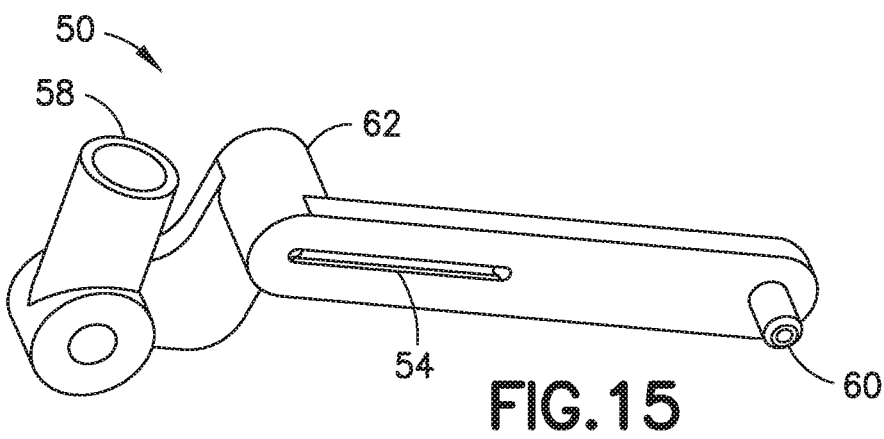

In another alternate embodiment, as illustrated in FIGS. 13-15, a flow channel member 50 includes a first fluid channel portion 52, a second fluid channel portion 54, and a third fluid channel portion 56 at different elevations with respect to the fill port 43. The embedded first, second, and third fluid channel portions 52, 54, 56 route medicament fluid flow in different plane locations, as further described below.

Specifically, a septum (not shown) is pierced to allow medicament to flow from the fill port 43. For example, a user inserts a syringe (not shown) to pierce the septum in the fill port 43 to inject the medicament inside the flow channel member 50 to a first port 58. The first port 58 includes a first passageway and a second passageway. The first passageway connects the fill port 43 to the reservoir (not shown) to fill the reservoir 4. The second passageway connects the reservoir to the first fluid channel portion 52.

Prior to the pumping operation, the flow channel member 50 is in a closed system with the pump 3 (not shown) being in a closed chamber and connected at a second port 60. Fluid enters the flow channel member 50 and travels to the pump 3 and the reservoir 4 thereby filling each of the first, second and third fluid channel portions 52, 54, 56. Subsequently, fluid can enter and fill the reservoir 4. As the reservoir 4 is being filled, the flow channel member 50 is primed by driving the fluid through the flow channel member 50 by the pump 3 over several cycles to remove any air present.

During the pumping operation, medicament is drawn from the reservoir by the pump 3 (not shown) that is connected at the second port 60 disposed at the other end of the flow channel member 50. When the pump 3 generates a suctioning pressure, medicament is pulled from the reservoir into the first fluid channel portion 52 on a top surface of the flow channel member 50. The medicament subsequently flows down a junction 62 (e.g. a through hole) of the flow channel member 50 and enters into a second fluid channel portion 54 disposed on a bottom surface of the flow channel member 50. The second fluid channel portion 54 is in fluid communication with the third fluid channel portion 56.

According to one embodiment, a through hole connects the second and third fluid channel portions 54, 56. According to another embodiment, each of the second and third fluid channel portions 54, 56 is deeper than one-half the thickness of the flow channel member 50, and adjacent ends of the second and third fluid channel portions 54, 56 overlap to establish fluid communication therebetween. Thus, the medicament flows from the second fluid channel portion 54 to the end of the third fluid channel portion 56 where a second port 60 connects to the pump 3.

As described above, FIGS. 13 and 14 illustrate the first fluid channel portion 52 and the third fluid channel portion 56 being disposed on a top surface of the flow channel member 50 and FIG. 15 illustrates the second fluid channel portion 54 being disposed on a bottom surface of the flow channel member 50. In this exemplary embodiment, the flow channel member 50 has three separate fluid channel covers 28 (not illustrated for clarity) encapsulating each of the first, second, and third fluid channel portions 52, 54, 56.

The flow channel member 50, or the like, advantageously provides for a variety of different component arrangements in the patch pump 1 to establish fluid communication through the interior of the patch pump 1. Specifically, the flow channel member 50 advantageously provides different fluid channel portions 52, 54, 56 at different elevations or different planar positions to provide flexibility when interfacing the medicament flow path with the various components in the patch pump 1. The use of the flow channel member 50, or the like, with fluid paths at different elevations also advantageously provides alternate routing capabilities for space optimization within the pump interior 12.

Figure 16:
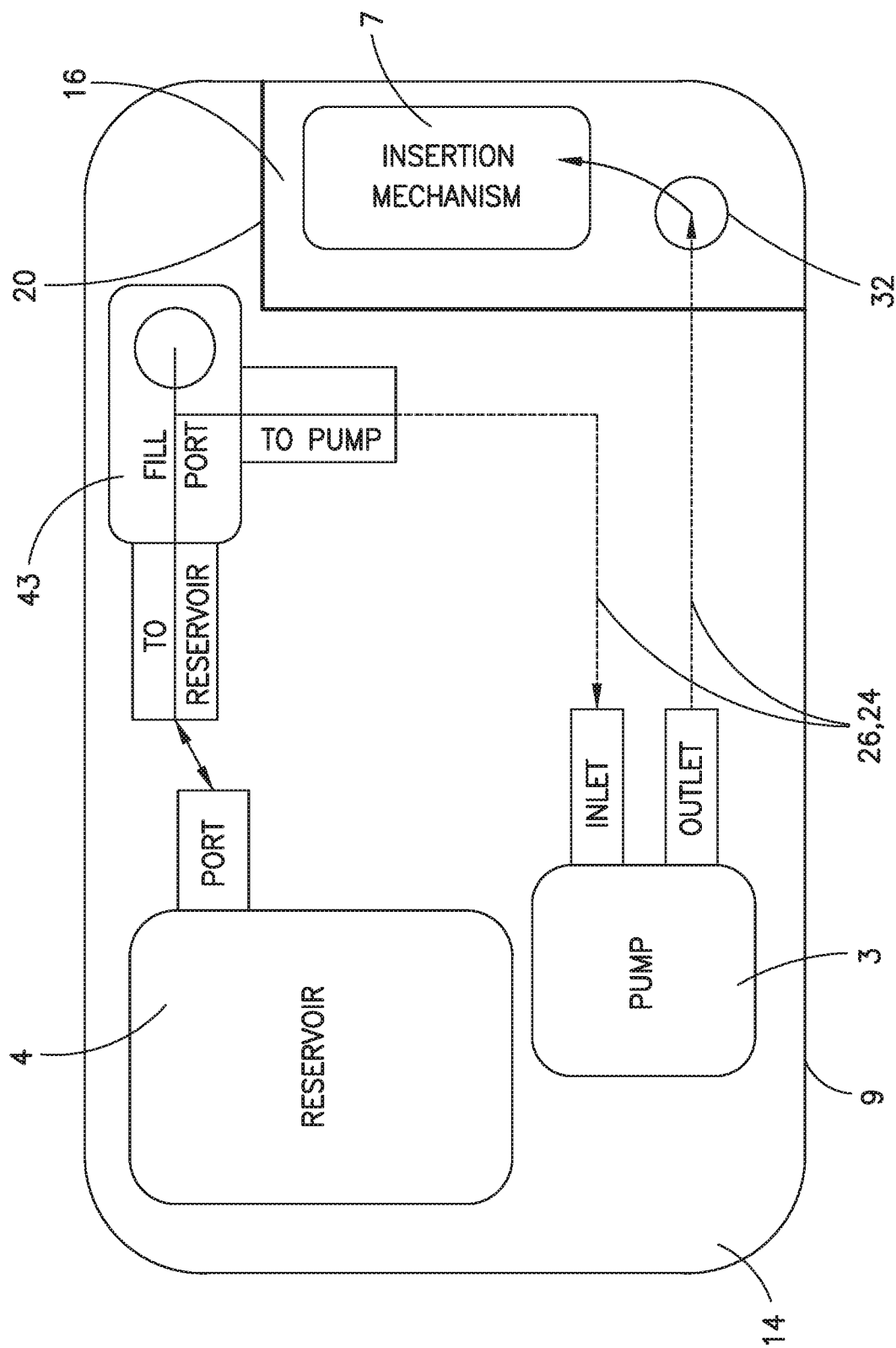
FIG. 16 is a schematic illustration of a medicament flow path of a patch pump in accordance with an embodiment of the present invention.

FIG. 16 is a schematic of an exemplary fluid path in the patch pump 1 in accordance with an illustrative embodiment of the present invention. Medicament enters the patch pump 1 via the fill port 43 to fill the reservoir 4. During operation of the patch pump 1, the pump 3 pulls medicament to exit the reservoir 4 into the fill port 43 via an auxiliary port, and subsequently flow to the inlet of the pump 3 via the second fluid channel 26. Next, the pump 3 drives the medicament to exit the pump 3, enter the first fluid channel 24, and flow to the receptacle 32 of the insertion mechanism 7. Finally, the insertion mechanism 7 receives the medicament from the receptacle 32 via tubing, for example, and delivers the medicament through the cannula 47 to the skin of the patient.

Although only a few embodiments of the present invention have been shown and described, the present invention is not limited to the described embodiments. Instead, it will be appreciated by those skilled in the art that changes may be made to these embodiments without departing from the principles and spirit of the invention. It is particularly noted that those skilled in the art can readily combine the various technical aspects of the various elements of the various exemplary embodiments that have been described above in numerous other ways, all of which are considered to be within the scope of the invention, which is defined by the appended claims and their equivalents.

What is claimed is:

1. A medicament delivery device comprising:
    a housing engaged to a base to form an interior therein, the interior includes:
        a fluid channel;
        a first internal region that is sealed from fluid ingress; and
        a second internal region that is not sealed from fluid ingress;
    wherein the fluid channel passes from a first position in the interior, to a second position outside the interior, and to a third position in the interior;
    the first position corresponds to the first internal region and the third position corresponds to the second internal region; and
    the medicament passes through the base from the first internal region to the second internal region.

2. The medicament delivery device according to claim 1, wherein the fluid channel includes a fluid channel passageway that extends through the base.

3. The medicament delivery device according to claim 2, wherein
    the fluid channel passageway includes
        a first fluid channel passageway disposed between the first and second positions; and
        a second fluid channel passageway disposed between the second and third positions.

4. The medicament delivery device according to claim 1, wherein the fluid channel is recessed into an external surface of the base.

5. The medicament delivery device according to claim 4, wherein a foil covers the fluid channel and a portion of the external surface of the base.

6. The medicament delivery device according to claim 5, wherein the foil comprises a clear film that is heat-sealed or heat staked to the external surface of the base.

7. The medicament delivery device according to claim 5, wherein the foil is laser welded to the external surface of the base.

8. The medicament delivery device according to claim 1, wherein the fluid channel includes a first fluid channel and a second fluid channel, the first and second fluid channels are recessed into an external surface of the base.

9. The medicament delivery device according to claim 8, wherein a first foil covers the first fluid channel and a second foil covers the second fluid channel.

10. The medicament delivery device according to claim 1, further comprising a barrier that separates the first internal region and the second internal region.

11. The medicament delivery device according to claim 1, wherein the interior comprises an enclosed space between the housing and the base.

12. The medicament delivery device according to claim 1, wherein the base includes a bottom external surface for orienting toward a skin of a patient, the bottom external surface of the base having the fluid channel integrally formed and disposed therein, the bottom external surface of the base being external to the device.

13. The medicament delivery device according to claim 1, wherein
the first internal region includes a pump or electronics; and
the second internal region includes an insertion mechanism or a cannula.

14. A medicament delivery device comprising:
a housing engaged to a base to form an interior therein, the interior including:
a first internal region that is sealed from fluid ingress, the first internal region including:
a reservoir for housing medicament;
a fill port in fluid communication with the reservoir;
a pump that controls flow of the medicament to the delivery mechanism; and
first and second fluid channels disposed in the base; and
a second internal region that is not sealed from fluid ingress, the second internal region including:
a delivery mechanism that delivers the medicament into a skin of a patient;
wherein the pump is in fluid communication with the delivery mechanism via the first fluid channel;
the second fluid channel passes from a first position in the interior, to a second position outside the interior, and to a third position in the interior;
the first position corresponds to the first internal region and the third position corresponds to the second internal region; and
the medicament passes through the base from the first internal region to the second internal region.

15. The medicament delivery device according to claim 14, wherein the fill port is in fluid communication with the pump via the second fluid channel.

16. The medicament delivery device according to claim 14, wherein the first or second fluid channel includes a fluid channel passageway that extends through the base to provide fluid communication between the interior and outside the interior.

17. The medicament delivery device according to claim 14, wherein the first fluid channel or the second fluid channel is recessed into an external surface of the base.

18. The medicament delivery device according to claim 17, wherein a foil covers a portion of the external surface of the base and the first fluid channel or the second fluid channel.

* * * * *